(12) United States Patent
Fukami et al.

(10) Patent No.: US 10,570,435 B2
(45) Date of Patent: Feb. 25, 2020

(54) CELL DETERMINATION METHOD, CELL DETERMINATION DEVICE AND CELL DETERMINATION PROGRAM

(71) Applicant: HAMAMATSU PHOTONICS K.K., Hamamatsu-shi, Shizuoka (JP)

(72) Inventors: Tadashi Fukami, Hamamatsu (JP); Hidenao Yamada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 158 days.

(21) Appl. No.: 15/760,348

(22) PCT Filed: Jun. 22, 2016

(86) PCT No.: PCT/JP2016/068549
§ 371 (c)(1),
(2) Date: Mar. 15, 2018

(87) PCT Pub. No.: WO2017/047190
PCT Pub. Date: Mar. 23, 2017

(65) Prior Publication Data
US 2018/0265908 A1  Sep. 20, 2018

(30) Foreign Application Priority Data
Sep. 16, 2015 (JP) ................. 2015-183067

(51) Int. Cl.
*G06K 9/00* (2006.01)
*C12Q 1/04* (2006.01)
(Continued)

(52) U.S. Cl.
CPC ............. *C12Q 1/04* (2013.01); *G01N 21/45* (2013.01); *G02B 21/361* (2013.01); *G02B 21/365* (2013.01); *G01N 2201/063* (2013.01)

(58) Field of Classification Search
None
See application file for complete search history.

(56) References Cited

U.S. PATENT DOCUMENTS 5,726,752 A * 3/1998 Uno ................. G01N 21/031
356/244
2004/0115683 A1* 6/2004 Medford ............. C12Q 1/6897
435/6.12
(Continued)

FOREIGN PATENT DOCUMENTS

JP    2013-249298 A    12/2013
JP    2014-039535 A    3/2014
(Continued)

OTHER PUBLICATIONS

Shugo Tohyama et al., "Distinct Metabolic Flow Enables Large-Scale Purification of Mouse and Human Pluripotent Stem Cell-Derived Cardiomyocytes," Cell Stem Cell, 2013, pp. 127-137, vol. 12.

(Continued)

*Primary Examiner* — Shervin K Nakhjavan
(74) *Attorney, Agent, or Firm* — Drinker Biddle & Reath LLP

(57) ABSTRACT

The present invention relates to a cell determination method for determining a cell type based on a content of glycogen in a cell, including: an acquisition step of acquiring optical path length data by measuring an optical path length of the cell; a calculation step of calculating an optical path length indicator correlated with the optical path length of the cell from the obtained optical path length data; a comparison step of comparing the calculated optical path length indicator with a threshold; and a determination step of determining whether the cell is a cell type having a high glycogen content (Continued)

in the cell or a cell type having a low glycogen content in the cell, based on the comparison result.

9 Claims, 11 Drawing Sheets

(51) Int. Cl.
  *G01N 21/45* (2006.01)
  *G02B 21/36* (2006.01)

(56) References Cited

U.S. PATENT DOCUMENTS

2009/0043171 A1* 2/2009 Rule ............... A61B 5/029 600/300
2009/0323076 A1* 12/2009 Li ............... A61B 5/0066 356/479

FOREIGN PATENT DOCUMENTS

| | | |
|---|---|---|
| JP | 2015-146747 A | 8/2015 |
| WO | WO-2012/147403 A1 | 11/2012 |
| WO | WO-2015/076042 A1 | 5/2015 |

OTHER PUBLICATIONS

Akinobu Suzuki et al., "Astrocyte-Neuron Lactate Transport Is Required for Long-Term Memory Formation," Cell, 2011, pp. 810-823, vol. 144, No. 5.

J. S. Lilleyman et al., "Periodic acid-Schiff reation and prognosis in lymphoblastic leukaemia," Journal of Clinical Pathology, 1979, pp. 158-161, vol. 32.

Mitsuru Inamura et al., "Efficient Generatin of Hepatoblasts From Human ES Cells and iPS Cells by Transient Overexpression of Homeobox Gene HEX," Molecular Therapy, 2011, pp. 400-407, vol. 19, No. 2.

Michael E. Rothenberg et al., "The Myc Connection: ES Cells and Cancer," Cell, 2010, pp. 184-186, vol. 143, No. 2.

Jonghwan Kim et al., "Embryonic stem cell-specific signatures in cancer: insights into genomic regulatory networks and implications for medicine," Genome Medicine, 2011, 3:75, 3(11)75, pp. 1-8.

Kohei Johkura et al., "Cytochemical and ultrastructural characterization of growing colonies of human embryonic stem cells," J. Anat. 2004, pp. 247-255, vol. 205, No. 4.

Stanislav O. Konorov et al., "Absolute quantification of Intracellular Glycogen Content in Human Embryonic Stem Cells with Raman Microspectroscopy," Analytical. Chemistry, 2011, pp. 6254-6258, vol. 83, No. 16.

Stanislav O. Konorov et al., "Raman Microscopy-Based Cytochemical investigations of Potential Niche-Forming Inhomogeneities Present in Human Embryonic Stem Cell Colonies," Applied Spectroscopy, 2011, pp. 1009-1016, vol. 65, No. 9.

Toyohiko Yamauchi et al., "Unstained Observation of Human iPS Cells under Quantitative Phase Microscope," Regenerative Medicine, Suppl., entire text, 2016, p. 223, vol. 15, including English translation.

International Preliminary Report on Patentability dated Mar. 29, 2018 for PCT/JP2016/068549.

* cited by examiner (A)

(B)

(A)

(B)

(A)

(B)

(A)

AREA OF COLONY (B)

AVERAGE OPTICAL THICKNESS OF COLONY

CELL DETERMINATION METHOD, CELL DETERMINATION DEVICE AND CELL DETERMINATION PROGRAM

TECHNICAL FIELD

The present invention relates to a cell determination method, a cell determination device, and a cell determination program.

BACKGROUND ART

Human-derived stem cells such as embryonic stem cells (ES cells) and induced pluripotent stem cells (iPS cells) have an ability to differentiate into many kinds of cells (pluripotency), and application thereof in the field of drug discovery and the field of medicine has been anticipated. A differentiation efficiency in differentiation induction from the stem cells into desired cells is largely dependent on the state of the stem cells as starting materials. That is, the efficiency of differentiation induction is lowered, unless the stem cells maintain pluripotency and keep an undifferentiated state. Thus, quality control of the stem cells is extremely important for industrial application of the stem cells, and the stem cells need to be monitored and their states need to be noninvasively determined.

It is known that in an undifferentiated state, the ES cells produce adenosine triphosphate (ATP) anaerobically by using the glycolytic system. When the cells are differentiated, ATP is mainly supplied by oxidative phosphorylation using the citric acid cycle (TCA cycle) (Non-Patent Literature 1). It is known that the dependency of the ES cells on glucose is higher than that of the differentiated cells, and the ES cells contain glycogen in their cytoplasm (Non-Patent Literature 2).

As a method for detecting glycogen, Periodic acid Schiff staining (PAS staining) is known (for example, Non-Patent Literature 2). In addition, Non-Patent Literature 3 reports quantifying glycogen content in cytoplasm of ES cells through Raman spectroscopic imaging.

CITATION LIST

Non Patent Literature

[Non-Patent Literature 1] Cell Stem Cell, 2013, vol. 12, pp. 127-137.
[Non-Patent Literature 2] J. Anat., 2004, vol. 205, pp. 247-255.
[Non-Patent Literature 3] Anal. Chem., 2011, vol. 83, pp. 6254-6258.

SUMMARY OF INVENTION

Problems to be Solved by the Invention

In the PAS stain method, cells cannot be noninvasively observed, since the cells need to be stained. In the Raman spectroscopic imaging described in Non-Patent Literature 3, cells can be observed without being stained. However, since the intensity of Raman scattering light is extremely weak, the intensity of illuminated light required for observation is strong, and there is concern of damaging the cells. Furthermore, in Raman spectroscopic imaging, it is difficult to analyze Raman scattering light specific to cells, from Raman scattering light derived from various components in a medium, and the cells in the medium cannot be observed as they are.

The present invention has been made under consideration of the above problems, and an object of the present invention is to provide a cell determination method, a cell determination device, and a cell determination program, with which a cell type can be noninvasively and easily determined based on a content of glycogen in a cell.

Means for Solving the Problems

The present invention provides a cell determination method for determining a cell type based on a content of glycogen in a cell, including an acquisition step of acquiring optical path length data by measuring an optical path length of the cell, a calculation step of calculating an optical path length indicator correlated with the optical path length of the cell from the obtained optical path length data, a comparison step of comparing the calculated optical path length indicator with a threshold, and a determination step of determining whether the cell is a cell type having a high glycogen content in the cell or a cell type having a low glycogen content in the cell, based on the comparison result.

The cell determination method of the present invention is based on the relationship found between a glycogen content in a cell and an optical path length: the greater the glycogen content in the cell, the longer the optical path length. Here, the "optical path length" is synonymous with "phase difference" or "optical thickness".

According to the cell determination method of the present invention, the cell type can be noninvasively and easily determined based on the content of glycogen in the cell. Furthermore, since the optical path length is used as an indicator, the cell in a medium can be determined as it is.

The acquisition step may be a step of acquiring the optical path length data by measuring the optical path length from a quantitative phase microscope image of the cell.

The cell determination method of the present invention may further include a measurement step of imaging an interference reflection microscope image of the cell and measuring an area of a colony from the interference reflection microscope image, in which in the calculation step, the optical path length indicator is calculated by dividing the total value of the optical path length data of cells included in the colony by the area of the colony. In this way, it is possible to more easily determine the cell in a colony unit.

In the cell determination method, the cell type having a high glycogen content in the cell is a pluripotent stem cell, and the cell type having a low glycogen content in the cell is a differentiated pluripotent stem cell, and the method may be used for distinguishing an undifferentiated pluripotent stem cell from a cell population of cultured pluripotent stem cells or distinguishing the differentiated pluripotent stem cell from the cell population.

An undifferentiated pluripotent stem cell is known to accumulate glycogen in the cell. As the pluripotent stem cell is differentiated, the glycogen content in the cell decreases. Therefore, the cell determination method of the present invention can be used, for example, for distinguishing undifferentiated pluripotent stein cells from a cell population of cultured pluripotent stem cells or distinguishing differentiated pluripotent stem cells from the cell population in subculturing of the pluripotent stem cells.

The present inventors found that undifferentiated induced pluripotent stem cells (iPS cells) accumulate glycogen in the cells, whereas differentiated iPS cells do not accumulate glycogen as the undifferentiated iPS cells do. Thus, it is possible to determine undifferentiated iPS cells and differentiated iPS cells with the cell determination method of the present invention.

The pluripotent stem cells may be induced pluripotent stem cells.

The present invention also provides a cell determination device including an acquisition means for acquiring optical path length data of a cell, a calculation means for calculating an optical path length indicator correlated with an optical path length of the cell from the acquired optical path length data, a comparison means for comparing the calculated optical path length indicator with a threshold, and a determination means for determining whether the cell is a cell type having a high glycogen content in the cell or a cell type having a low glycogen content in the cell, based on the comparison result. The cell determination device may further include a second acquisition means for acquiring an interference reflection microscope image of the cell or data obtained by binarizing the image. By further including the second acquisition means, determination can be more easily performed in a colony unit.

Furthermore, the present invention provides a cell determination program arranged to make a computer function as an acquisition means for acquiring optical path length data of a cell, a calculation means for calculating an optical path length indicator correlated with an optical path length of the cell from the acquired optical path length data, a comparison means for comparing the calculated optical path length indicator with a threshold, and a determination means for determining whether the cell is a cell type having a high glycogen content in the cell or a cell type having a low glycogen content in the cell, based on the comparison result. The cell determination program may be further arranged to make the computer function as a second acquisition means for acquiring an interference reflection microscope image of the cell or data obtained by binarizing the image.

The cell determination program may be provided as a computer-readable storage medium storing the cell determination program.

Effects of the Invention

According to the present invention, a cell type can be noninvasively and easily determined based on a content of glycogen in a cell.

BRIEF DESCRIPTION OF DRAWINGS

FIG. 8(A) is a quantitative phase microscope image of a colony. FIG. 8(B) is a fluorescence microscope image of the colony which is fluorescently stained with an anti-Nanog antibody.

EMBODIMENTS FOR CARRYING OUT THE INVENTION

Figure 1:
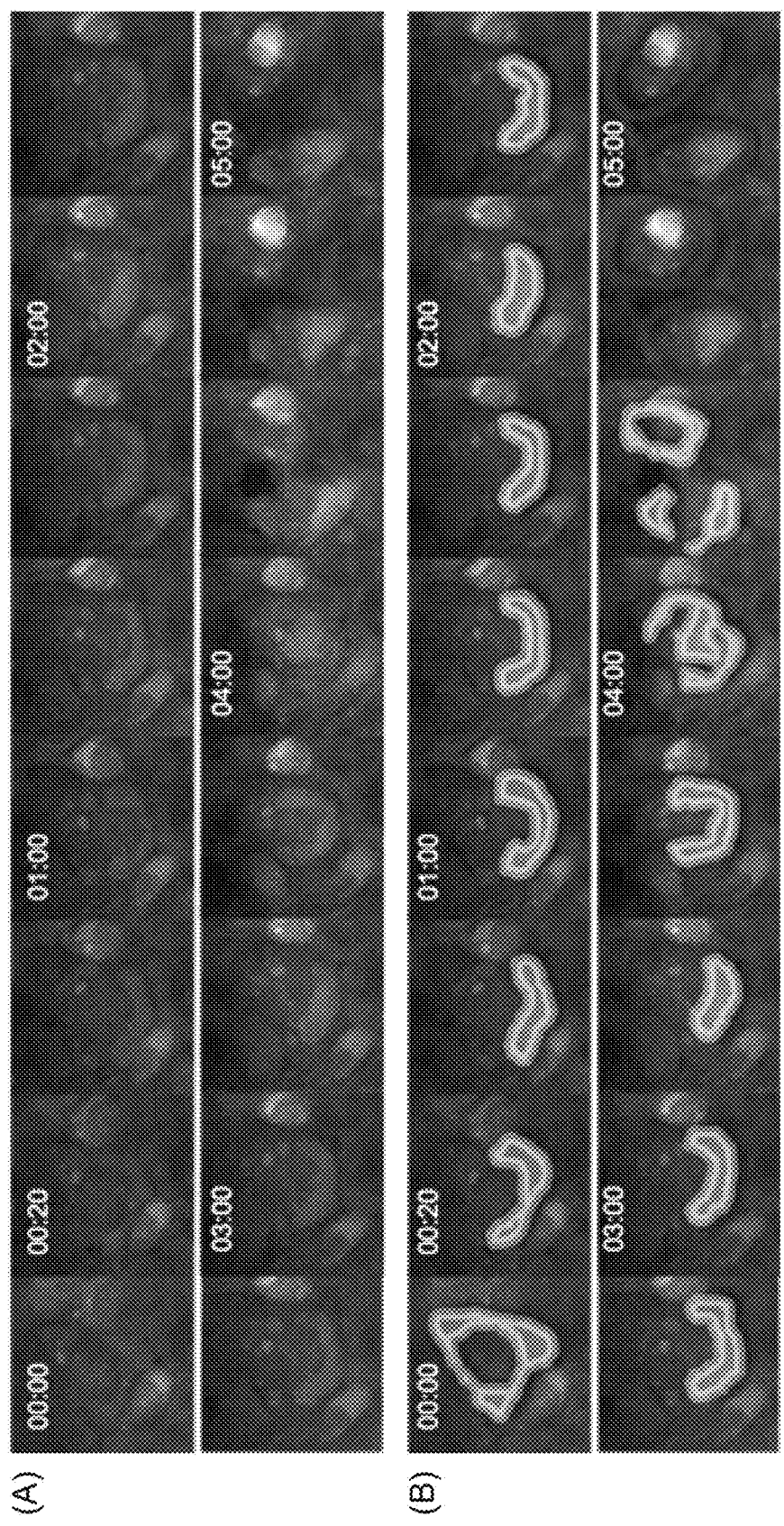
FIG. 1(A) shows photographs showing the results obtained by observing an aspect of cell division of iPS cells over time using a quantitative phase microscope.
FIG. 1(B) shows diagrams in which regions of high brightness (high optical path length regions) in (A) are highlighted.

Hereinafter, preferred embodiments of the present invention will be described in detail with reference to the drawings depending on the case, however, the present invention is not limited to the following embodiments. In the drawings, the same or corresponding parts are designated by the same reference signs, and redundant description will be omitted as appropriate.

The present invention is based on the obtainment of a novel finding that there is a correlative relationship between an optical path length (brightness) of a cell observed using a quantitative phase microscope and a content of glycogen in the cell. First, description will be made on this novel finding.

FIG. 1(A) shows photographs showing the results obtained by observing an aspect of cell division of iPS cells over time using a quantitative phase microscope. The photographs were taken every 20 minutes. FIG. 1(B) shows diagrams in which regions of high brightness (high optical path length regions) in the photographs of FIG. 1(A) are highlighted. As shown in FIG. 1, a nucleolus is lost (00:20), and a high optical path length region present in cytoplasm is aggregated (00:40), divided into two (04:00), and distributed to two cells (05:00), as the cell division progresses. According to the observation by the present inventors, this high optical path length region always emerges during cell division. In a case where a chromonema is focused on during the cell division, one or two high optical path length regions emerge in the cell as an endoplasmic reticulum-like structure, in a chromonema-associated manner.

Figure 2:
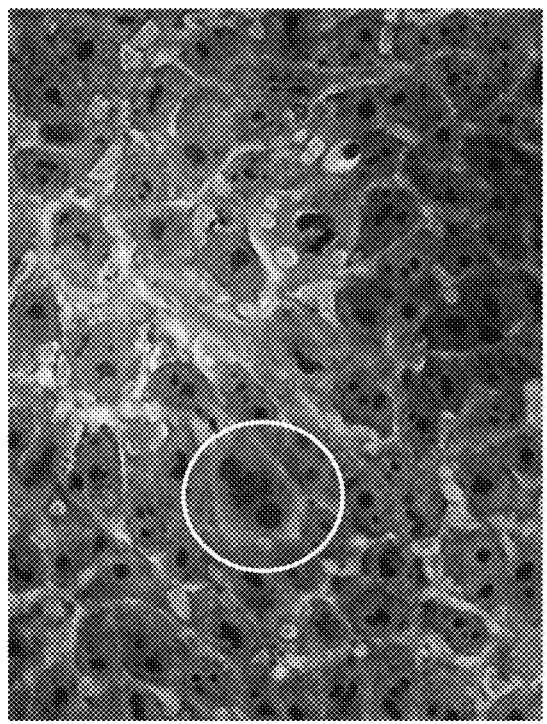
FIG. 2(A) is a photograph showing the result of PAS staining of a colony of iPS cells.
FIG. 2(B) is a photograph showing the result obtained by observing the colony of iPS cells using a quantitative phase microscope.
Figure 2:
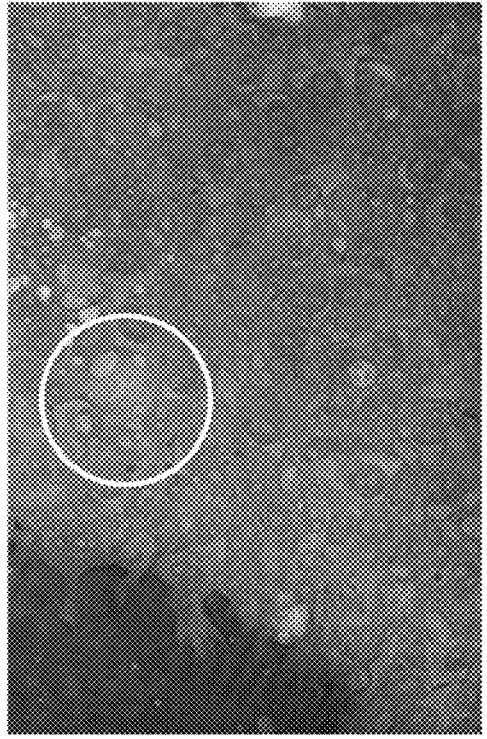

FIG. 2(A) is a photograph showing the result of PAS staining of a colony of iPS cells. FIG. 2(B) is a photograph showing the result obtained by observing the colony of iPS cells using a quantitative phase microscope. A cell in a mitotic stage is circled in FIGS. 2(A) and (B). As shown in FIG. 2(A) and FIG. 2(B), the same position as the high optical path length region described above is stained by PAS staining. Furthermore, since the high optical path length region is lost due to a treatment with amylase (not shown in the drawings), it is presumed that glycogen is accumulated in the high optical path length region.

Figure 3:
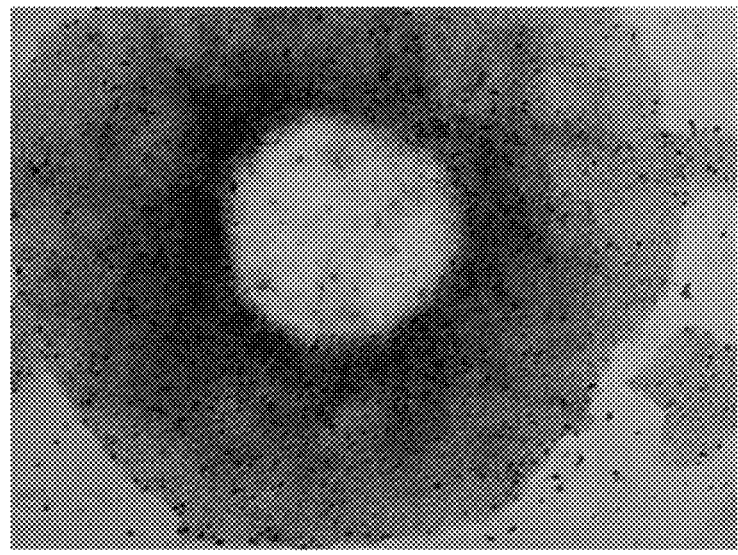
FIG. 3(A) is a photograph showing the result of PAS staining of a colony of iPS cells.
FIG. 3(B) is a photograph showing the result of alkaline phosphatase staining (AP staining) of the same colony as in FIG. 3(A).
Figure 3:
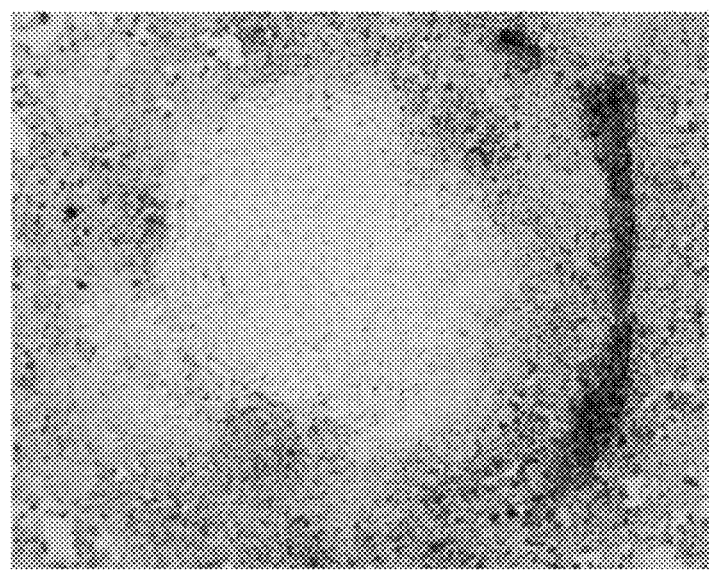

FIG. 3(A) is a photograph showing the result of PAS staining of a colony of iPS cells. FIG. 3(B) is a photograph showing the result of alkaline phosphatase staining (AP staining) of the same colony as in FIG. 3(A). Undifferentiated iPS cells are stained by AP staining. As can be understood from FIGS. 3(A) and (B), the differentiated cells (center portion) that are not stained by AP staining are also not stained by PAS staining, and the undifferentiated iPS cells stained by AP staining are stained by PAS staining.

From the above results, it is understood that a cell with a high content of glycogen has a longer optical path length (brightness is high in a quantitative phase microscope image) than that of a cell with a low content of glycogen.

Regarding the above-described novel finding, the present inventors hypothesized the following. That is, the optical path length (brightness) observed under the quantitative phase microscope is calculated by multiplying an "actual thickness of a cell" by a "refractive index difference between cell-medium". It is considered that the actual thickness of a cell and refractive indices of a medium and the cell do not vary greatly, and thus, in a case where a slight difference in refractive index is generated, it is considered that this difference is observed as a great change in the optical path length. Since the refractive index of glycogen is 1.69, which is greater than the refractive index of a general biological macromolecule (1 to 1.5), it is considered that as the accumulated amount (content) of glycogen is greater, a greater change in a length of the optical path length (level of brightness) is observed.

[Cell Determination Method]

The cell determination method of the present invention determines a cell type based on a content of glycogen in a cell.

(Cell Type which is Target for Determination)

The cell determination method of the present embodiment performs determination based on the glycogen content, and thus, in a cell line in which a cell type having a high glycogen content and a cell type having a low glycogen content are mixed with each other, or there is a possibility of these cell types being mixed with each other (collectively referred to as a "mixed cell line"), the cell determination method of the present embodiment can be used to determine the cell type having a high glycogen content and/or the cell type having a low glycogen content.

Examples of the cell type having a high glycogen content and the cell type having a low glycogen content include a cell type having a high glycogen content such as a cell type which produces ATP, an energy source of a cell, mainly using an anaerobic glycolytic pathway and a cell type having a low glycogen content such as a cell type which produces ATP, an energy source of a cell, mainly using oxidative phosphorylation in the TCA cycle.

Specific examples of the mixed cell line include, but not limited to, a pluripotent stem cell culture system (a culture system of which the object is to maintain pluripotency), a cell culture system in the case of differentiating pluripotent stem cells into somatic cells of liver, kidney, heart, pancreas, and nerve, a culture system of cells derived from a myocardial tissue, a liver tissue, and a nerve tissue, a mixed culture system of nerve cells/astroglia cells, and a cell culture system of lymphocytes of leukemia patients.

In the pluripotent stem cell culture system, there is a possibility that undifferentiated pluripotent stem cells (cell type having a high glycogen content) and differentiated pluripotent stem cells (with a low glycogen content) are mixed with each other. The cell determination method of the present embodiment may be used to distinguish undifferentiated pluripotent stem cells from a cell population of the cultured pluripotent stem cells or distinguish differentiated pluripotent stem cells from the cell population. In this way, the quality control (maintaining of the undifferentiated state) of cells being subcultured can be noninvasively and easily performed. In addition, in a case where the pluripotent stem cells are differentiated into somatic cells, the differentiated pluripotent stem cells can be noninvasively and easily distinguished in regenerative medicine and the like.

In the myocardial cell culture system, there is a possibility that fetus myocardial cells (cell type having a high glycogen content) and adult myocardial cells (with a low glycogen content) are mixed with each other. The cell determination method of the present embodiment may be used to distinguish fetus myocardial cells from a cell population of the cultured myocardial cells or distinguish adult myocardial cells from cells from the cell population. In this way, the cell determination method of the present embodiment is effective in evaluating quality of matured myocardial cells such as a myocardial sheet in regenerative medicine.

The nerve cells are known to consume glucose directly, and the astroglia cells accumulate excess glucose as glycogen in the cells (Cell, 2011, vol. 144, no. 5, pp. 810-823). Accordingly, the cell determination method of the present embodiment may be used for distinguishing nerve cells from a cell population of the cultured nerve cells and astroglia cells or distinguishing astroglia cells from the cell population.

In classification and determination of progression of leukemia, PAS staining is used (J. Clin. Pathol., 1979, vol. 32, pp. 158-161). Therefore, the cell determination method of the present embodiment may be used for the classification or the determination of progression of leukemia.

(Optical Path Length Data)

An acquisition step is a step of acquiring optical path length data by measuring an optical path length of a cell. The optical path length data of the cell can be obtained as, for example, "phase difference" or an "optical thickness" by imaging the cell using a quantitative phase microscope or a phase difference microscope. The optical path length data may be acquired in a single cell or may be acquired in a plurality of cells (for example, a cell colony unit or a unit of visual field of a microscope).

The target cells in the cell determination method of the present embodiment are usually cultured cells. Since the determination results are not easily affected by components in a medium, in the acquisition step, the optical path length data may be acquired by measuring the optical path length of the cells in the culture medium. Operation becomes remarkably easy, since cells in a culture medium can be used the target for measurement.

(Optical Path Length Indicator)

A calculation step is a step of calculating an optical path length indicator correlated with the optical path length of the cell from the optical path length data obtained in the acquisition step. The optical path length indicator is correlated with the optical path length of the cell. In other words, as long as a correlative relationship between an optical path length of a cell and content of glycogen in the cell can be used in determination, the acquired optical path length data may be used as it is as the optical path length indicator, or an indicator (for example, an average value) calculated based on optical path length data acquired in a plurality of cells may be used as the optical path length indicator.

The optical path length indicator may be, for example, a value calculated by dividing the total value of the optical path length data acquired in a cell population included in a certain colony by the area of the colony (an optical path length per unit area of the certain colony). The area of the colony can be measured, for example, by imaging an interference reflection microscope (IRM) image, binarizing the IRM image, and distinguishing between a portion of a culture substrate to which cells are attached and a portion of the culture substrate to which cells are not attached.

The optical path length indicator may also be calculated by dividing the total value of the optical path length data acquired in a cell population included in one visual field of the microscope by the area of the cell population included in the visual field (an optical path length per unit cell area in a certain visual field).

(Threshold)

A comparison step is a step of comparing the optical path length indicator calculated in the calculation step with a threshold. The threshold can be appropriately set according to the cell type which is the target for determination, culture condition, and the like. For example, in a case where undifferentiated pluripotent stem cells or differentiated pluripotent stem cells in a pluripotent stem cell culture system are used as the target for determination, the acquisition step and the calculation step described above are performed in the pluripotent stem cell culture system, so as to calculate the optical path length indicator. The undifferentiated pluripotent stem cells and the differentiated pluripotent stem cells are distinguished from each other in the same pluripotent stem cell culture system according to a conventional method (for example, AP staining or anti-Nanog antibody staining). Based on these results, the threshold with which the undifferentiated pluripotent stein cells and the differentiated pluripotent stem cells can be distinguished from each other is set in advance.

(Determination Step)

A determination step is a step of determining whether the cell is a cell type having a high glycogen content in the cell or a cell type having a low glycogen content in the cell, based on the comparison result obtained in the comparison step.

In a case where the optical path length indicator is an indicator positively correlated with the optical path length of the cell (a case where, as the optical path length of the cell becomes longer, the optical path length indicator becomes greater), determination is made as follows:

(i) in a case where the optical path length indicator is greater than or equal to the threshold, it is determined that the cell is a cell type having a high glycogen content in the cell, or (ii) in a case where the optical path length indicator is less than the threshold, it is determined that the cell is a cell type having a low glycogen content in the cell.

In a case where the optical path length indicator is an indicator negatively correlated with the optical path length of the cell (a case where, as the optical path length of the cell becomes longer, the optical path length indicator becomes smaller), determination is made as follows:

(iii) in a case where the optical path length indicator exceeds the threshold, it is determined that the cell is a cell type having a low glycogen content in the cell, or (iv) in a case where the optical path length indicator is less than or equal to the threshold, it is determined that the cell is a cell type having a high glycogen content in the cell.

[Cell Determination Device]

In one embodiment, the cell determination device is combined with an optical path length measurement device to be used as a cytometer. As the optical path length measurement device, for example, a quantitative phase microscope or a phase difference microscope can be used.

Figure 4:
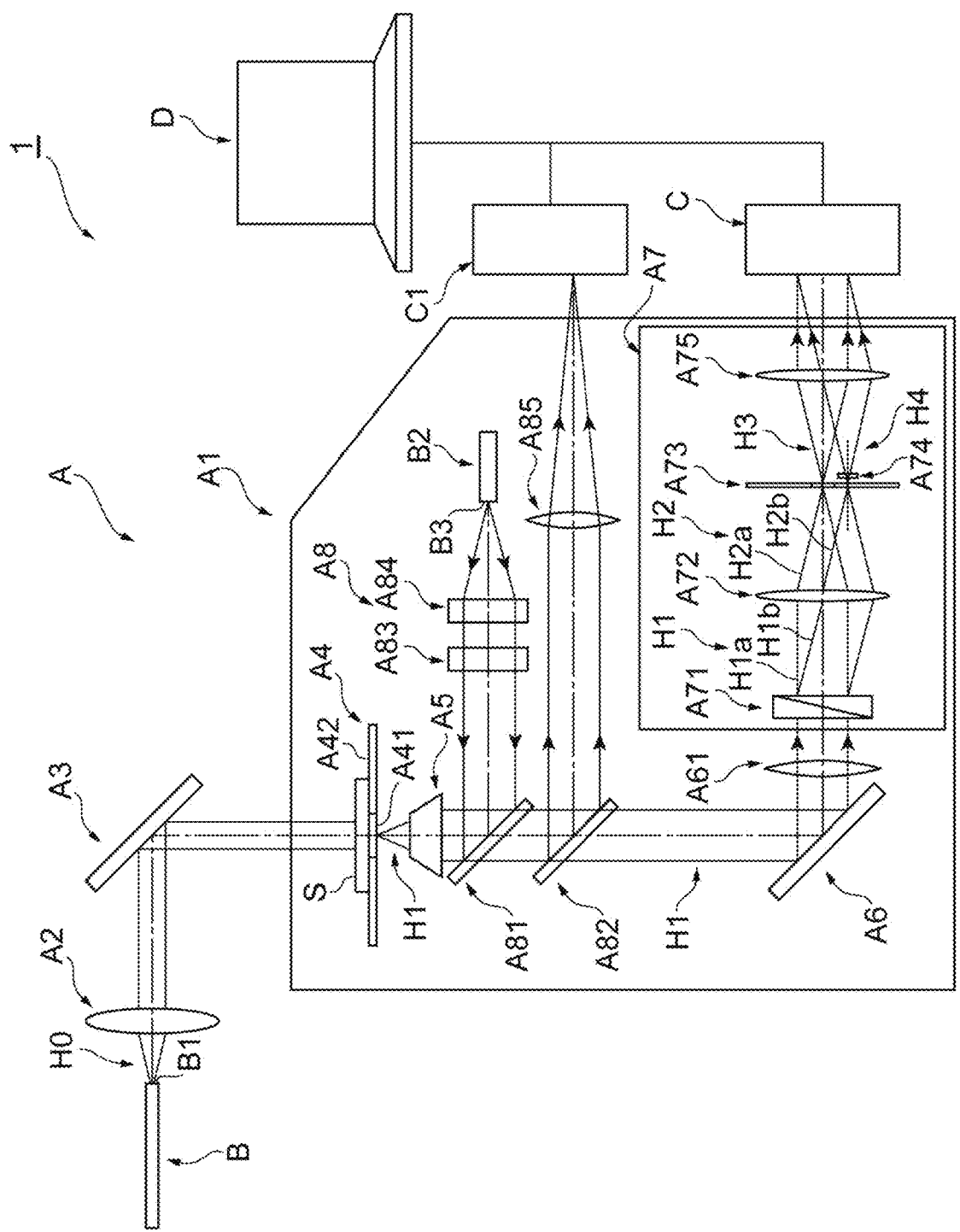
FIG. 4 is a constitution diagram of a cytometer according to one embodiment.

FIG. 4 is a constitution diagram of the cytometer according to one embodiment. A microscope system A in which an optical system of an interference reflection microscope and an optical system of a quantitative phase microscope are combined and a cell determination device D mainly constitute a cytometer 1 shown in FIG. 4. The optical system of the quantitative phase microscope may solely constitute the microscope system A. The area of a single cell, the area of a colony, and the area of a cell in a visual field can be measured together by fluffier including the optical system of the interference reflection microscope in the microscope system A.

(Quantitative Phase Microscope)

The optical system of the quantitative phase microscope includes, on the light incidence side, a lens A2 facing an end face B1 on the exit side of an optical fiber B which guides irradiation light H0 (laser light) from a light exit part not shown in the drawing and a reflection part A3 which reflects the irradiation light H0 transmitted through the lens A2. On the light exit side of the optical system of the quantitative phase microscope, an imaging unit C such as a CCD camera which obtains an image by imaging an interference fringe (not shown in the drawing, the same applies hereinafter) generated by an optical interference part A7 is provided.

A microscope A includes a microscope main body A1 which at least has a sample stage A4 for supporting a measurement sample S, an objective lens A5, a reflection part A6, and the optical interference part A7. As shown in FIG. 4, the microscope main body A1 may further have an optical system A8 of the interference reflection microscope.

The sample stage A4 is, for example, a nearly plate-shaped stage including a light transmission part A41 in the center, through which light can be transmitted, and a mounting surface A42, on the surface facing upward, on which the measurement sample S can be mounted. By irradiating the mounting surface A42 with light from above in a state in which the measurement sample S is placed on the mounting surface A42, light transmitted through the measurement sample S (light to be measured H1) is transmitted through the light transmission part A41 and is directed toward the objective lens A5. The light transmission part A41 may be formed of a member capable of transmitting light, such as glass, or may be simply a hole. The objective lens A5 enlarges the incident light to be measured H1 based on, for example, the operation of an operation part (not shown in the drawing) at a predetermined magnification set by the operation, and allows the light to be measured to exit as parallel light. The reflection part A6 is, for example, a total reflection mirror which totally reflects the light to be measured H1 from the objective lens A5 and enables the light to be introduced into the optical interference part A7. The optical interference part A7 includes a light splitting element A71 which splits the light to be measured H1 into two light rays of H1a and H1b, a collective lens A72 which converts the light to be measured H1 (H1a and H1b) exit from the light splitting element A71 into converging light H2 (H2a and H2b), a spatial filter A73 which is placed at a position where the converging light H2 converges, and a complex lens A75 which generates an interference fringe by superimposing object light H3 and reference light H4 transmitted through the spatial filter A73. Here, the light splitting element A71 is configured using a diffraction grating. In addition, the light splitting element A71 may be a polarized light splitting element which splits the light into two light rays having different polarization directions. In this case, the optical interference part A7 includes the light splitting element A71 which splits the light to be measured H1 into two light rays, H1*a* and H1*b*, having different polarization directions, the collective lens A72 which performs the conversion into the converging light H2 (H2*a* and H2*b*), the spatial filter A73 which is placed at a position where the converging light H2 converges, the object light H3 and the reference light H4 transmitted through the spatial filter A73, a half-wave plate A74 placed on the exit side of the spatial filter A73, and the complex lens A75 which generates an interference fringe by superimposing the object light H3 and the reference light H4 of which the polarization directions are aligned by the half-wave plate A74. Alternatively, instead of placing the half-wave plate A74 on the exit side of the spatial filter A73, a polarizer may be placed to align the polarization directions of the object light H3 and the reference light H4.

(Interference Reflection Microscope)

The optical system A8 of the interference reflection microscope measures light (the light to be measured H1) reflected by the measurement sample S by irradiating the mounting surface A42 with light from below in a state in which the measurement sample S is placed on the mounting surface A42. The optical system of the interference reflection microscope includes, on the light incidence side, a bandpass filter A84 and an aperture slit A83 facing an end face B3 on the exit side of an optical fiber B2 which guides irradiation light (laser light) from a light source (not shown in the drawing), and a reflection part A81 (for example, a beam splitter) that reflects the irradiation light transmitted through the bandpass filter A84 and the aperture slit A83. The light source is configured of a white LED or the like. On the light exit side of the optical system of the interference reflection microscope, a reflection part A82 (for example, a dichroic mirror) which reflects the light to be measured H1 from the objective lens 5 and the reflection part A81 and guide the light to a collective lens A85 and an imaging unit C1 such as a CCD camera which obtains an image by imaging the light to be measured converged by the collective lens A85 are provided.

(Cell Determination Device)

Figure 5:
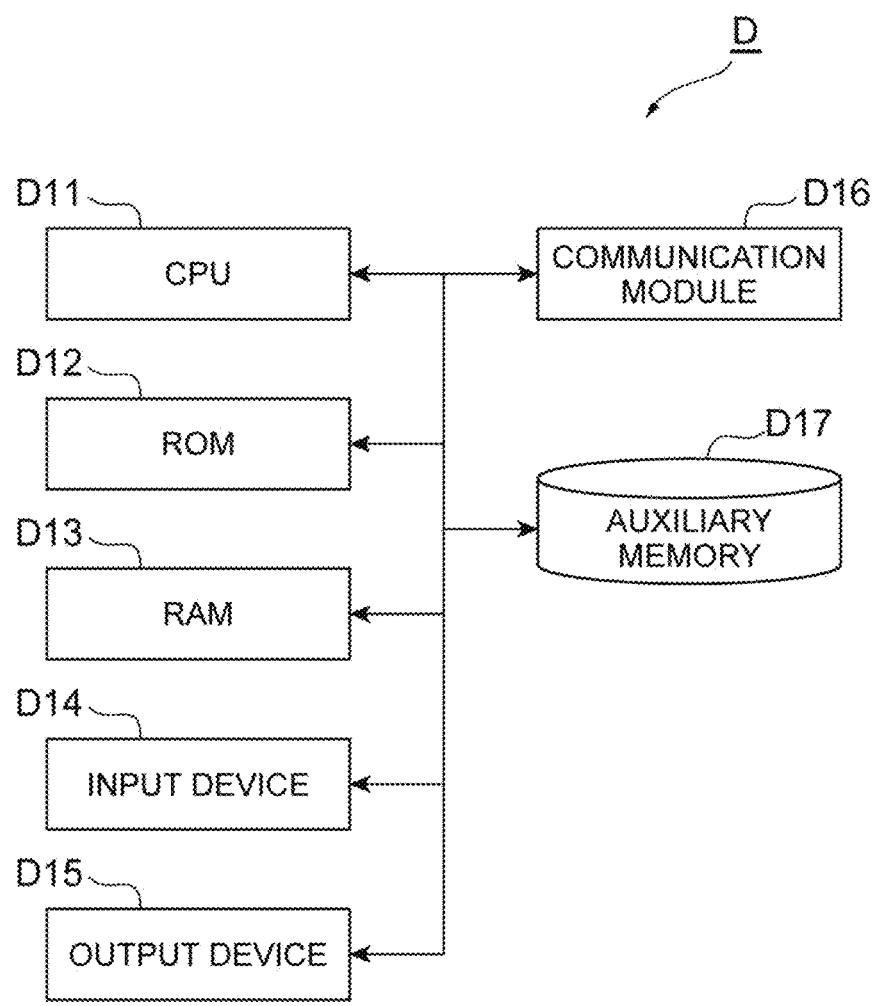
FIG. 5 is a schematic diagram showing a hardware constitution of a cell determination device according to one embodiment.

The constitution of the cell determination device D will be described. FIG. 5 is a schematic diagram showing a hardware constitution of the cell determination device D according to one embodiment, and FIG. 6 is a schematic diagram showing a functional constitution of the cell determination device D according to one embodiment.

As shown in FIG. 5, a conventional computer which physically includes a CPU D11, a main memory such as ROM D12 and RAM D13, an input device D14 such as a keyboard and a mouse, an output device D15 such as a display, a communication module D16 such as a network card for transmission and reception of data in communication with other devices such as the imaging unit C, an auxiliary memory D17 such as a hard disk, and the like constitutes the cell determination device D. Each function of the cell determination device D described below can be realized by loading a given computer software on hardware such as CPU D11, ROM D12, and RAM D13, activating the input device D14, the output device D15, and the communication module D16 under control of the CPU D11, and reading and writing the data in the main memory D12 and D13 as well as the auxiliary memory D17.

Figure 6:
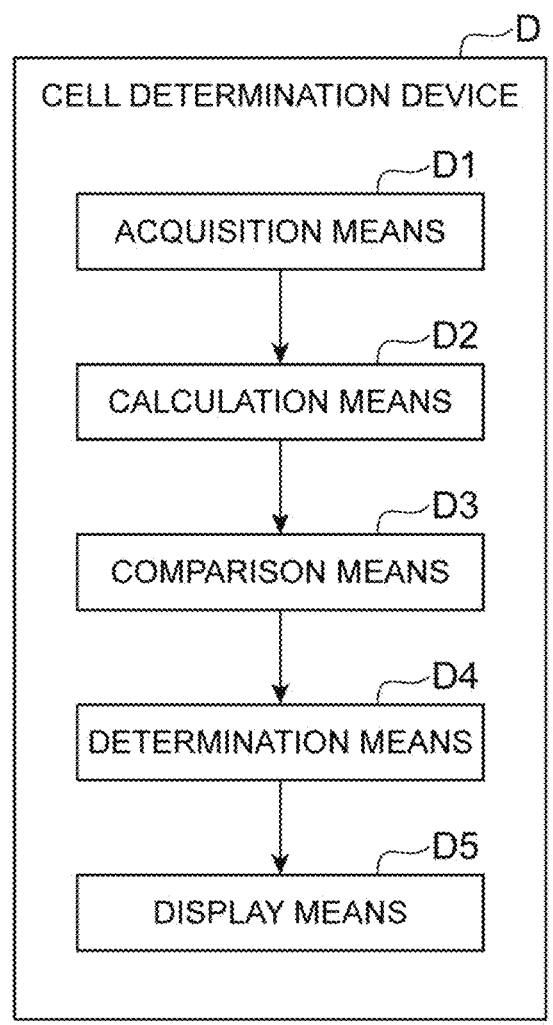
FIG. 6 is a schematic diagram showing a functional constitution of the cell determination device according to one embodiment.

As shown in FIG. 6, the cell determination device D includes acquisition means D1, calculation means D2, comparison means D3, determination means D4, and display means D5, as functional components.

The acquisition means D1 acquires optical path length data from a quantitative phase microscope image photographed using the imaging unit C. The acquisition means D1 also functions as a means for acquiring an interference reflection microscope image data photographed using the imaging unit C1 or data obtained by binarizing the image. The calculation means D2 calculates the optical path length indicator described above from the acquired optical path length data. The comparison means D3 compares the calculated optical path length indicator with a threshold. The threshold stored in the auxiliary memory D17 of the cell determination device D or the like in advance may be read. The determination means D4 determines the cell type based on the comparison result. The display means D5 displays the determination result.

[Cell Determination Program]

A cell determination program allows a computer to function as the acquisition means D1, the calculation means D2, the comparison means D3, the determination means D4, and the display means D5 describe above. By loading the cell determination program on the computer, the computer can function as the cell determination device D. The cell determination program is provided, for example, by being stored in a computer-readable storage medium. The storage medium may be a non-transitory storage medium. The storage medium is exemplified by a storage medium such as a flexible disc, CD, and DVD, a storage medium such as a ROM, a semiconductor memory, or the like.

(Cell Determination Method)

Figure 7:
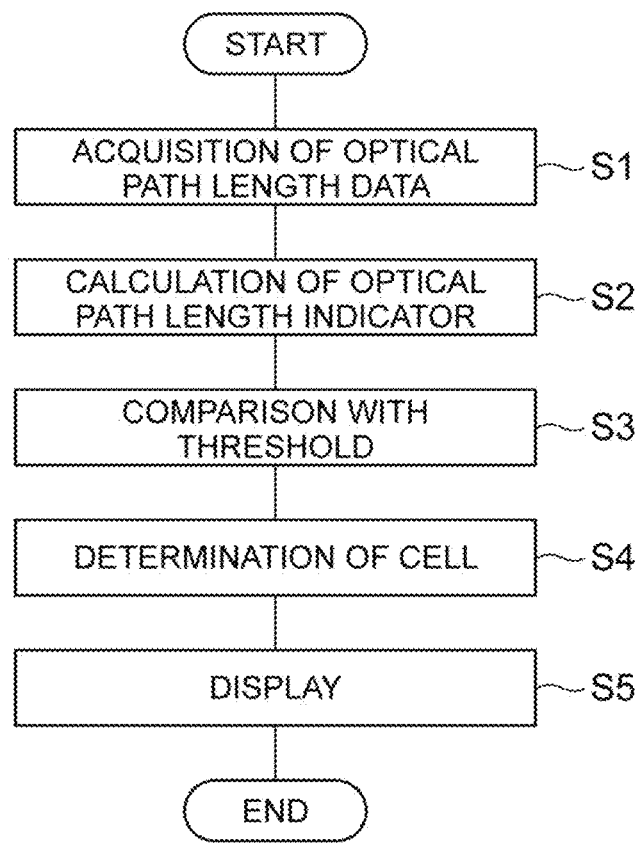
FIG. 7 is a flow chart of a cell determination method according to one embodiment.

The cell determination method carried out using the cell determination device D will be described. FIG. 7 is a flow chart of the cell determination method. With the cell determination method carried out using the cell determination device D, it is possible to quantitatively and automatically determine whether the target cell is a cell type having a high glycogen content in the cell or a cell type having a low glycogen content in the cell, with high accuracy.

[Acquisition Step S1]

First, the acquisition means D1 acquires the optical path length data of the cell from the imaging unit C. In a case where the optical path length indicator is, for example, an optical path length per unit area of a certain colony, or in a case where the optical path length indicator is an optical path length per unit cell area in a certain visual field, an IRM image of the colony or the visual field from which the optical path length data is acquired may be acquired by the acquisition means D1.

[Calculation Step S2]

Next, the optical path length indicator is calculated from the optical path length data acquired by the calculation means D2. In a case where the optical path length indicator is, for example, an optical path length per unit area of a certain colony, or in a case where the optical path length indicator is an optical path length per unit cell area in a certain visual field, the step may also include calculating a cell area (for example, a colony area) from the IRM image of the colony or the visual field from which the optical path length data is acquired.

[Comparison Step S3]

The comparison means D3 then compares the optical path length indicator calculated in the calculation step S2 with the threshold and extracts the result. The comparison means D3 may also include reading the threshold stored in the auxiliary memory D1.7 or the like in advance.

[Determination Step S4]

Next, the determination means D4 determines whether the cell is a cell type having a high glycogen content in the cell or a cell type having a low glycogen content in the cell, based on the comparison result extracted in the comparison step S3. The determination means D4 performs determination as follows, based on the comparison result obtained in the comparison step S3.

A case where the optical path length indicator is an indicator positively correlated with the optical path length of the cell (a case where, as the optical path length of the cell becomes longer, the optical path length indicator becomes greater);

(i) in a case where the optical path length indicator is greater than or equal to the threshold, it is determined that the cell is a cell type having a high glycogen content in the cell, or (ii) in a case where the optical path length indicator is less than the threshold, it is determined that the cell is a cell type having a low glycogen content in the cell.

A case where the optical path length indicator is an indicator negatively correlated with the optical path length of the cell (a case where, as the optical path length of the cell becomes longer, the optical path length indicator becomes smaller);

(iii) in a case where the optical path length indicator exceeds the threshold, it is determined that the cell is a cell type having a low glycogen content in the cell, or (iv) in a case where the optical path length indicator is less than or equal to the threshold, it is determined that the cell is a cell type having a high glycogen content in the cell.

[Display Step S5]

Next, the display means D5 displays the determination result obtained in the determination step S4. For example, whether the cell is a cell type having a high glycogen content in the cell or a cell type having a low glycogen content in the cell is displayed by the display means D5.

EXAMPLE

An example of determining cells that have undergone differentiation and undifferentiated iPS cells in subculturing of iPS cells with the cell determination method of the present invention will be described. However, the present invention is not limited to the following example.

Figure 8:
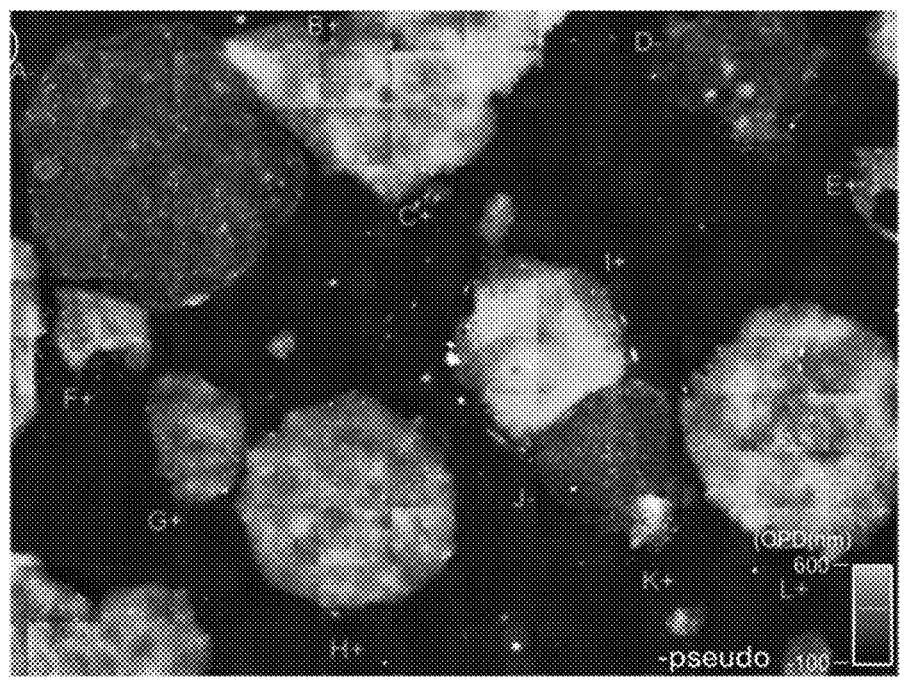
FIG. 8 shows photographs showing an example of determining cells that have undergone differentiation and undifferentiated iPS cells in subculturing of iPS cells.
Figure 8:
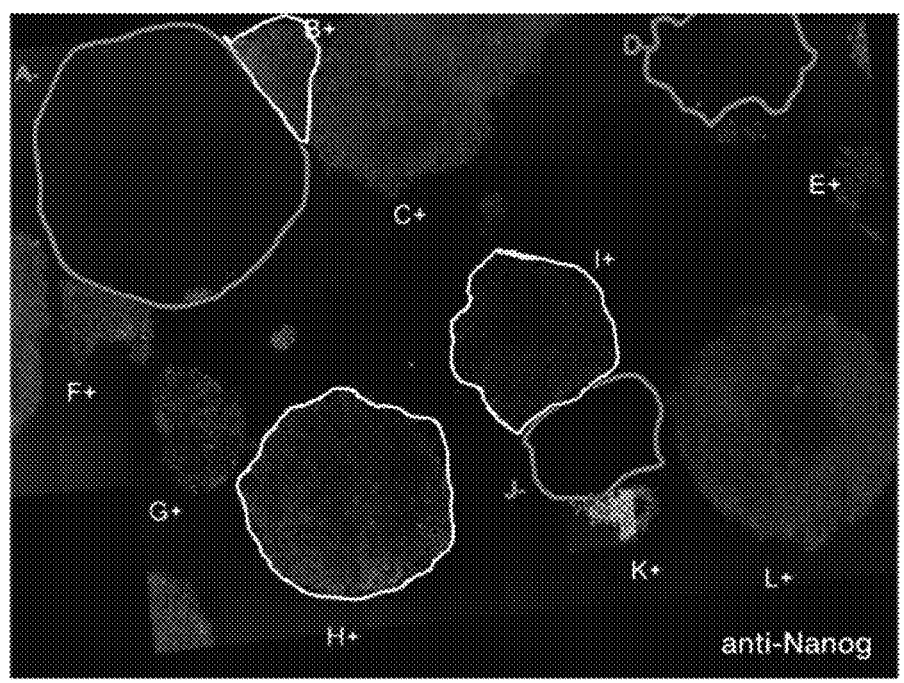

FIG. 8 shows photographs showing an example of determining cells that have undergone differentiation and undifferentiated iPS cells in subculturing of iPS cells (253G1 strain). FIG. 8(A) is a quantitative phase microscope image of a colony formed by culturing for three days after the subculturing. A plurality of colonies are included in one visual field. Higher brightness (optical path length is long) is displayed whiter. FIG. 8(B) is a fluorescence microscope image of the same colony as in FIG. 8(A) which has been immunostained with an anti-Nanog antibody. The colony that is stained by the immunostaining (fluorescence is observed) indicates undifferentiated iPS cells. Since immunostaining is not a quantitative method, the result does not perfectly conform with the brightness shown in FIG. 8(A); however, it is confirmed that the colonies with high brightness (optical path length is long) in FIG. 8(A) are immunostained with the anti-Nanog antibody. As can be clearly seen from FIG. 8, in a case where the optical path length (brightness) observed with a quantitative phase microscope exceeds a predetermined value, the cells or the colonies can be determined to be undifferentiated iPS cells or colonies.

Figure 9:
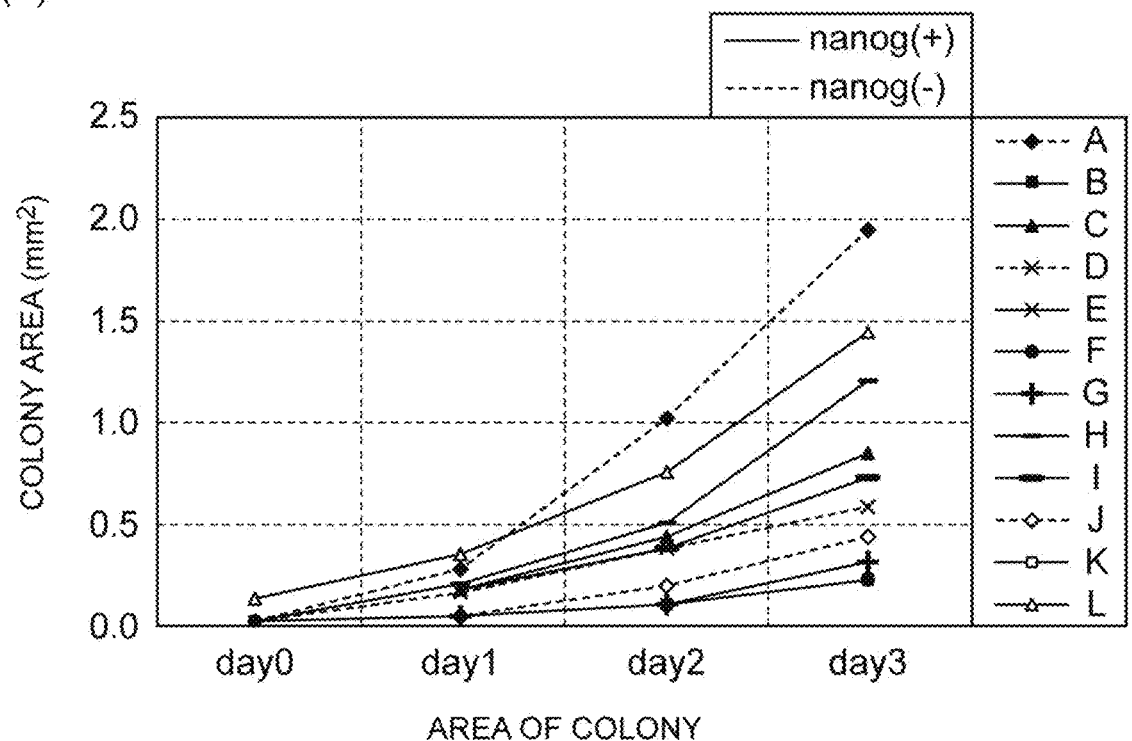
FIG. 9(A) is a graph showing the area of each colony shown in FIG. 8.
FIG. 9(B) is a graph showing an optical path length (average optical thickness of the colony) per unit area of each colony shown in FIG. 8.
Figure 9:
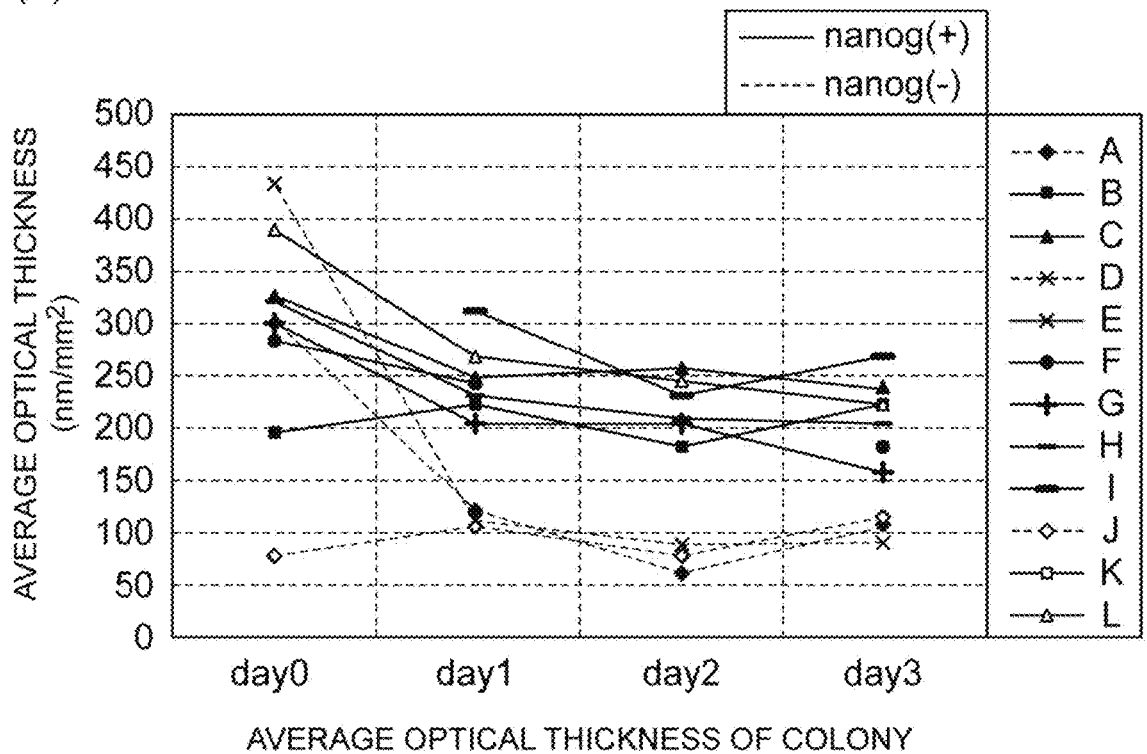

FIG. 9(A) is a graph showing the area of each colony shown in FIG. 8. The area of each colony is calculated by binarizing an IRM image separately imaged with an interference reflection microscope through image processing and distinguishing between a portion of a culture substrate to which cells are attached and a portion of the culture substrate to which cells are not attached. The horizontal axis indicates culture time. It is found that the colony area increases as the culture time is longer. FIG. 9(B) is a graph showing an optical path length (average optical thickness of the colony: $nm/mm^2$) per unit area of each colony shown in FIG. 8. From the first day (day 1) of culturing when the adhesion state of the cells was stabilized, there was a clear difference in the average optical thickness of the colony between a colony of undifferentiated iPS cells (Nanog-positive colony) and a colony of differentiated iPS cells (Nanog-negative colony). Specifically, the average optical thicknesses of colonies A, D and J (Nanog-negative colonies) in FIG. 8 were 90 to 120 $nm/mm^2$, and the average optical thicknesses of colonies B, C, F, H and L (Nanog-positive colonies) in FIG. 8 were 200 to 250 $nm/mm^2$. Therefore, by setting the threshold between, for example, 155 to 165 $nm/mm^2$, it is possible to determine the colony of undifferentiated iPS cells and the colony of differentiated iPS cells.

Figure 10:
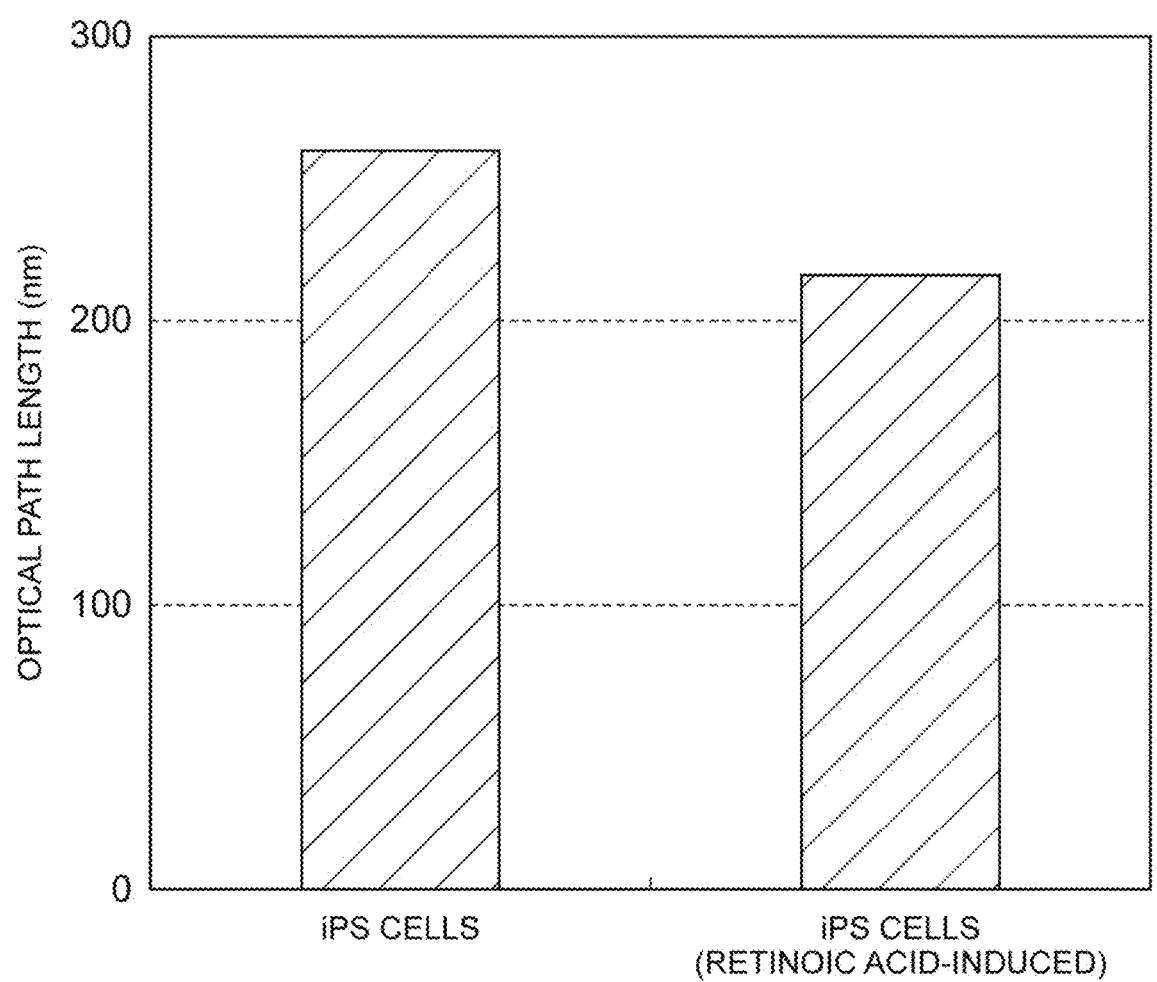
FIG. 10 is a graph showing optical path lengths of undifferentiated iPS cells and iPS cells induced to be differentiated.
Figure 11:
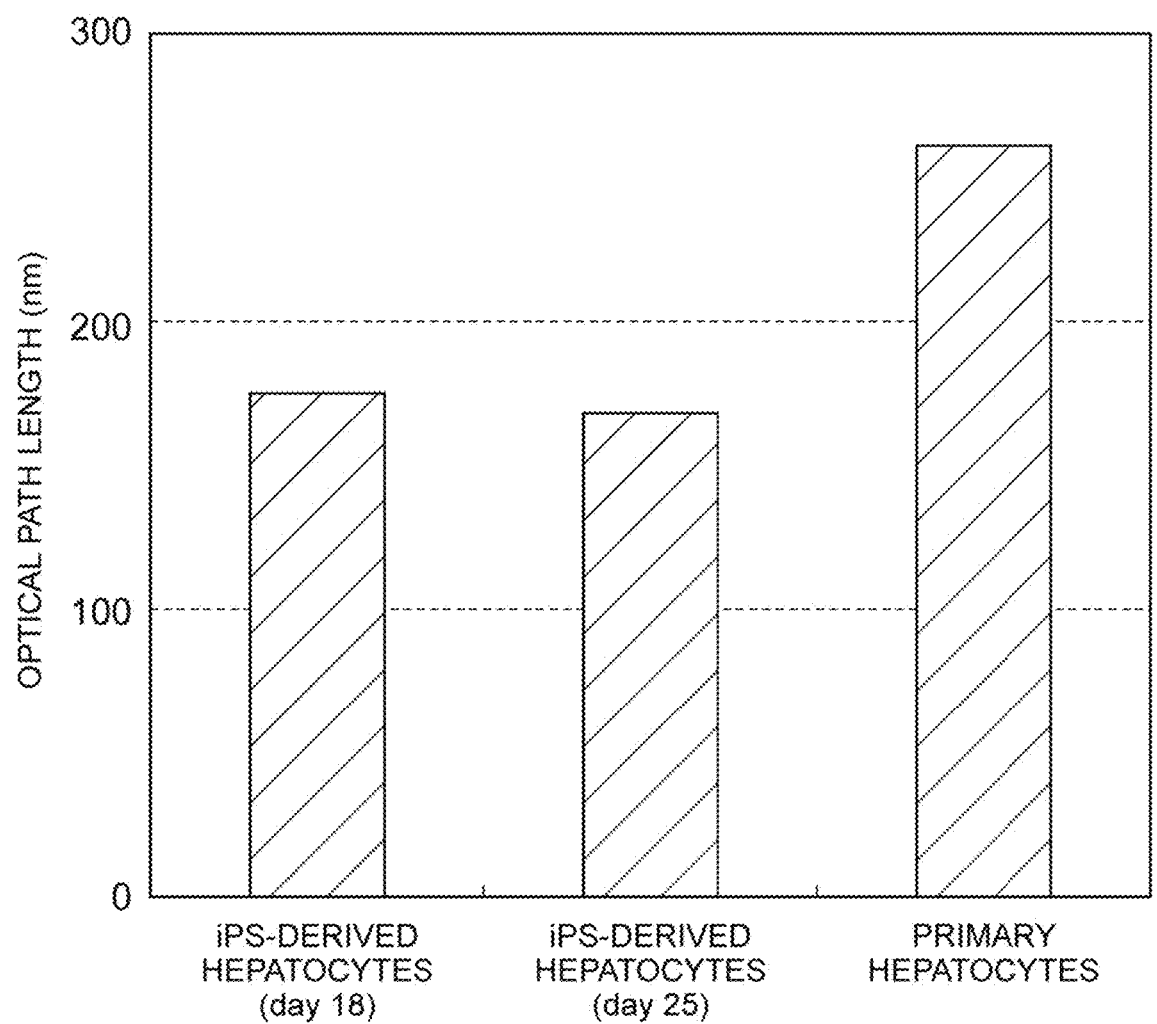
FIG. 11 is a graph showing optical path lengths of iPS cell-derived hepatocytes (initiation of differentiation) and matured hepatocytes.

FIG. 10 is a graph showing optical path lengths of undifferentiated iPS cells and iPS cells induced to be differentiated. FIG. 11 is a graph showing optical path lengths of iPS cell-derived immature hepatocytes and matured hepatocytes. The optical path lengths shown in FIG. 10 and FIG. 11 indicate brightness (optical path length) extracted from quantitative phase microscope images.

The "iPS cells" and the "iPS cells (retinoic acid-induced)" shown in FIG. 10 and the "iPS-derived hepatocytes" and the "primary hepatocytes" shown in FIG. 11 are cultured in the following manner.

The "iPS cells" were cultured in the following way. A human living fibroblast-derived iPS cell strain (253G1 strain) was seeded at 10 to 20 colonies/dish on a 35 mm-diameter plastic bottom dish with antireflection coating, coated with MATRIGEL (registered trademark) basement membrane matrix (manufactured by Becton, Dickinson and Company; hereinafter, referred to as a "substrate"), and was cultured in a feeder-less manner using a synthetic medium for culturing pluripotent stem cells (mTeSR (registered trademark) 1; manufactured by STEMCELL Technologies Inc.; hereinafter, referred to as a "synthetic medium"). The size of one colony was approximately 200 μm. The cells were cultured until the third day after the seeding. The synthetic medium was exchanged once a day. A quantitative phase microscope image was imaged on the third day after the seeding to measure the optical path length.

As for the "iPS cells (retinoic acid-induced)", on the second day after the seeding of the "iPS cells", the medium was exchanged with a synthetic medium to which 12.5 μM retinoic acid was added, and the cells were further cultured for four days. Generally, retinoic acid is used as a reagent for inducing differentiation. A quantitative phase microscope image was imaged on the fourth day after the addition of retinoic acid to measure the optical path length.

The "iPS-derived hepatocytes" are hepatocytes induced from the "iPS cells" according to the procedure described in Non-Patent Literature (Molecular Therapy, 2011, vol. 19, no. 2, pp. 400 to 407). Quantitative phase microscope images were imaged on the $18^{th}$ day and $25^{th}$ day after the initiation of the induction to measure the optical path length.

The "primary hepatocytes" were cultured using a BD Gentest Human Hepatocyte (catalog no. 454550, lot no. 299) strain available from Becton, Dickinson and Company and Hepato-STIM medium (manufactured by Becton, Dickinson and Company). A quantitative phase microscope image was imaged on the first day after seeding to measure the optical path length.

As shown in FIG. 10, the optical path length (brightness) decreases by adding retinoic acid, which is known as a reagent for inducing differentiation, compared to the optical path length of the "iPS cells" which are undifferentiated pluripotent stem cells. In addition, as shown in FIG. 11, the optical path length of the immature hepatocytes (day 18 and day 25) in the initial state of being induced to be differentiated into hepatocytes from iPS cells decreased in the course of the differentiation induction, however, as the iPS cells matured into hepatocytes, the optical path length increased due to accumulation of glycogen.

REFERENCE SIGNS LIST 1 cytometer
A microscope system
A1 microscope main body
B optical fiber
imaging unit
D cell determination device
D1 acquisition means
D2 calculation means
D3 comparison means
D4 determination means
D5 display means

The invention claimed is:

1. A cell determination method for determining a cell type based on a content of glycogen in a cell, comprising:
 an acquisition step of acquiring optical path length data by measuring an optical path length of the cell;
 a calculation step of calculating an optical path length indicator correlated with the optical path length of the cell from the obtained optical path length data;
 a comparison step of comparing the calculated optical path length indicator with a threshold; and
 a determination step of determining whether the cell is a cell type having a high glycogen content in the cell or a cell type having a low glycogen content in the cell, based on the comparison result.

2. The cell determination method according to claim 1, wherein the acquisition step is a step of acquiring the optical path length data by measuring the optical path length from a quantitative phase microscope image of the cell.

3. The cell determination method according to claim 1, further comprising:
 a measurement step of imaging an interference reflection microscope image of the cell and measuring an area of a colony from the interference reflection microscope image,
 wherein in the calculation step, the optical path length indicator is calculated by dividing the total value of the optical path length data of cells included in the colony by the area of the colony.

4. The cell determination method according to claim 1, wherein the cell type having a high glycogen content in the cell is a pluripotent stem cell, and the cell type having a low glycogen content in the cell is a differentiated pluripotent stem cell, and
 the method is used for distinguishing an undifferentiated pluripotent stem cell from a cell population of cultured pluripotent stem cells or distinguishing the differentiated pluripotent stem cell from the cell population.

5. The cell determination method according to claim 4, wherein the pluripotent stem cell is an induced pluripotent stem cell.

6. A cell determination device comprising:
 an acquisition means for acquiring optical path length data of a cell;
 a calculation means for calculating an optical path length indicator correlated with an optical path length of the cell from the acquired optical path length data;
 a comparison means for comparing the calculated optical path length indicator with a threshold; and
 a determination means for determining whether the cell is a cell type having a high glycogen content in the cell or a cell type having a low glycogen content in the cell, based on the comparison result.

7. The cell determination device according to claim 6, further comprising:
 a second acquisition means for acquiring an interference reflection microscope image of the cell or data obtained by binarizing the image.

8. A non-transitory computer-readable storage medium storing a cell determination program arranged to make a computer function as:
 an acquisition means for acquiring optical path length data of a cell;
 a calculation means for calculating an optical path length indicator correlated with an optical path length of the cell from the acquired optical path length data;
 a comparison means for comparing the calculated optical path length indicator with a threshold; and
 a determination means for determining whether the cell is a cell type having a high glycogen content in the cell or a cell type having a low glycogen content in the cell, based on the comparison result.

9. The non-transitory computer-readable storage medium according to claim 8, further arranged to make the computer function as:
 a second acquisition means for acquiring an interference reflection microscope image of the cell or data obtained by binarizing the image.

* * * * *